United States Patent [19]

Schindler et al.

[11] Patent Number: 5,776,932

[45] Date of Patent: *Jul. 7, 1998

[54] 1,3,5-TRISUBSTITUTED INDAZOLE DERIVATIVES, PROCESSES FOR PREPARING, AND FOR PHARMACOLOGICAL TREATMENT THEREWITH

[75] Inventors: Rudolf Schindler, Dresden; Ilona Fleischhauer, Offenbach; István Szelényi, Schwaig, all of Germany

[73] Assignee: Arzneimittelwerk Dresden G.m.b.H., Radebeul, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 821,740

[22] Filed: Mar. 20, 1997

[30] Foreign Application Priority Data

Mar. 20, 1996 [DE] Germany .................. 196 10 882.9

[51] Int. Cl.[6] .................. A61K 31/535; A61K 31/505; A61K 31/47; A61K 31/44; A61K 31/42; A61K 31/415; C07D 413/12; C07D 413/06; C07D 409/12; C07D 409/06; C07D 403/12; C07D 403/06; C07D 401/12; C07D 401/06; C07D 231/56

[52] U.S. Cl. .................. 514/235.2; 514/259; 514/274; 514/314; 514/338; 514/378; 514/394; 514/418; 544/116; 544/284; 544/310; 546/176; 546/275.7; 548/24.7; 548/305.1; 548/361.5

[58] Field of Search .................. 514/235.2, 259, 514/274, 314, 338, 378, 394, 418; 548/361.5, 247, 305.1; 544/116, 284, 310; 546/176, 275.7

[56] References Cited

U.S. PATENT DOCUMENTS

| 4,537,966 | 8/1985 | Murray .................. 546/120 |
| 4,859,692 | 8/1989 | Bernstein et al. .................. 514/394 X |
| 5,334,597 | 8/1994 | Prasit et al. .................. 514/314 X |
| 5,436,247 | 7/1995 | Sohda et al. .................. 514/259 |

OTHER PUBLICATIONS

File HCAPLUS on STN®, Chemical Abstracts Service, (Columbus, Ohio), Accession No. 1996:489898; Meanwell, N.A. et al. Bioorg. Med. Chem. Lett., 6(14), 1641–1646 (1996), abstract. 1996.

File HCAPLUS on STN®, Chemical Abstracts Service, (Columbus, Ohio), Accession No. 1973:43355; Corsi, G. Boll. Chim. Farm., 111(9), 566–72 (1972), abstract. 1973.

File HCAPLUS on STN®, Chemical Abstracts Service, (Columbus, Ohio), Accession No. 1971:87046; Kametani, T. et al. Org. Mass Spectrom., 4(Suppl.), 395–404 (1970), abstract. 1971.

*Primary Examiner*—Michael G. Ambrose
*Attorney, Agent, or Firm*—Schweitzer Cornman Gross & Bondell LLP

[57] ABSTRACT

1,3,5-trisubstituted indazole derivatives of the formula

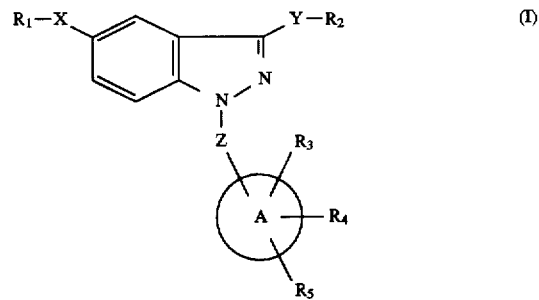

wherein R1 is H, (b) a $C_{1-6}$ straight or branched, substituted or unsubstituted alkyl residue, (c) a $C_{3-7}$ cycloalkyl residue, (d) an unsustituted or substituted phenyl, naphthyl, anthranyl, or fluorenyl residue, (e) a quinolin-2-ylmethoxy, or pyridin-2-ylmethoxy residue; X is O, or a —NH, —NH—(C=O)—NH—, —NH—(C=O)—O—, —NH—(C=O)—, or —NH—CH$_2$—(C=O)— residue; Y is O, or S; $R_2$ is H; Z is a SO, SO$_2$, —(CH$_2$)$_p$—, —(CH$_2$)$_p$—O—, —O—(CH$_2$)$_p$—, —(CH$_2$)$_p$—(C=O)—, —(C=O)—(CH$_2$)$_p$—, —(CH$_2$)$_p$—(C=O)—NH—, —NH—(C=O)—(CH$_2$)$_p$—, —(CH$_2$)$_p$—CHOH—, —CHOH—(CH$_2$)$_p$—, —(CH$_2$)$_p$—CH=CH—, or —CH=CH—(CH$_2$)$_p$— residue, wherein p is between 1 and 6; A is a phenyl, naphthyl, anthranyl, fluorenyl, thiophenyl, pyridinyl, isoxazolyl, benzimidazolyl, benz[1,3]dioxolyl, pyrimidyl, pyrimidine-2,4-dionyl, quinolinyl, quinoxazolinyl, morpholinyl, or pyrrolidinyl residue; and, $R_3$, $R_4$, and $R_5$, the same or different, are defined in the specification; and pharmaceutically acceptable salts, stereoisomers, racemates, racemic modifications, and enantiomers thereof. The invention also relates to specific compounds, processes for preparing and for treating an allergic, asthmatic, inflamed condition of a host, or for modulating the immune system of a host.

13 Claims, No Drawings

1,3,5-TRISUBSTITUTED INDAZOLE DERIVATIVES, PROCESSES FOR PREPARING, AND FOR PHARMACOLOGICAL TREATMENT THEREWITH

FIELD OF THE INVENTION

The invention relates to novel 1,3,5-trisubstituted indazole derivatives and to processes for their preparation, and to pharmacological treatment therewith as antiallergics such as antiasthmatics, and antiinflammatories for treating conditions such as rhinitis, dermatitis, conjunctivitis and enteritis, and as immunomodulators.

BACKGROUND OF THE INVENTION

Polyunsaturated fatty acids, such as arachidonic acid, act in the human metabolism as substrates for the enzymatically catalyzed formation of physiologically important eicosanoids, e.g. prostaglandins and leukotrienes, which are also collectively known by the name slow reacting substances of anaphylaxis (SRS-A). The formation of prostaglandins is catalyzed by cyclooxygenase (also known as "prostaglandin synthetase") and the formation of leuktrienes is catalyzed by 5-lipoxygenase.

Leukotrienes are known to be responsible for the development of allergic reaction, for anaphylactic shock, bronchoconstriction and inflammation in allergic diseases, such as rhinitis, dermatitis, conjunctivitis, enteritis, etc., and for other pathogenic effects. Compounds are therefore being sought which inhibit 5-lipoxygenase as specifically as possible and thereby prevent the formation of leukotrienes.

There are some substituted indazole derivatives known with a variety of substituents, but they have different pharmacodynamic action than was sought for purposes of the present invention. Bendazac [(1-benzyl-1H-indazole-3-yl) oxyl] acetic acid, is a typical compound of the prior art and having a predominantly antiinflammatory action. U.S. Pat. No. 3,470,194 describes the synthesis of bendazac. Corsi in Boll. Chim. Farm. 111, 566–572 (1972), and Giannangeli et al. in Boll. Chim. Farm. 121, 465–474 (1982) have reported on the metabolites of bendazac and European patent No. A 191,520 describes the use of [(1-benzyl-5-hydroxy-1H-indazole-3-yl) oxy] acetic acids for the treatment of colds.

European patent No. B 382,276 describes 1-benzyl-3-hydrozymethyl indazoles with an analgesic action.

Baiocchi et al. in Synthesis 1978 (9), 633–648, provide a survey of syntheses and properties of 1H-indazole-3-ols, especially 5-methoxy-1H-indazole-3-ol.

Mosti et al. in I Farmaco Ed. Sci. vol. 43 (10), 763–774 (1988) describe the preparation of indazole-4-yl derivatives having an analgesic and antiinflammatory action.

Pfannstiel et al. in Ber. Dtsch. Chem. Ges. 75 (9), 1096–1107 (1942) have reported on the preparation of nitro-1H-indazole-3-ols.

European patent No. A 290,145 discloses 1,3,6-trisubstituted indazoles which are leukotriene antagonists.

Aran et al. in J. Chem. Soc., Perkin Trans. I, 1993, 1119–1127, and in Liebigs Ann. 1995, 817–824, describe 1-substituted 5-nitro-1H-indazole-3-ols and their cytostatic activity against HeLa cells.

Schmutz et al. in Helv. Chim. Acta vol. 47(7), 1986–1996 (1964), and Ketami et al. in J. Heterocycl. Chem. 7, 807–834 (1970) have reported on the synthesis of 1-benzyl-1H-indazole-3-ols.

Corsi et al. in Ann. Chim. (Rome) 60, 246–258 (1970) describe the preparation of 3-mercaptoindazoles.

European patent No. A 199,543 discloses benzoheterocyclic alkanoic acids which are leukotriene antagonist and which can be used for example, in the treatment of allergic asthma, eczema and psoriasis.

Canadian patent No. 2,116,621 discloses heterocyclic N-chloroethyl-carbonic acid or -carbamic acid derivatives with an antineoplastic action, but without systemic toxicity or mutagenicity, for the treatment of tumors.

Canadian patent No. 4,224,363 discloses nitroindazoles for the dyeing of hair and keratin and other natural and synthetic fibers.

European patent No. A 448,206 discloses aryloxy- or acylamino-indazoles or -benzimidazoles as herbicides.

Because of the numerous side effects of the available preparations, the lack of remedial success and their so far too unspecific physiological activity, there is also a great need for compounds with a high efficacy and safety for the treatment of asthmatic diseases.

DETAILED DESCRIPTION OF THE INVENTION

It is an object of the invention to provide novel compounds with an improved antiasthmatic, antiallergic, antiinflammatory and immunomodulating activity, and a higher therapeutic index.

According to the present invention, these novel compounds are 1,3,5-trisubsituted indazoles of the formula:

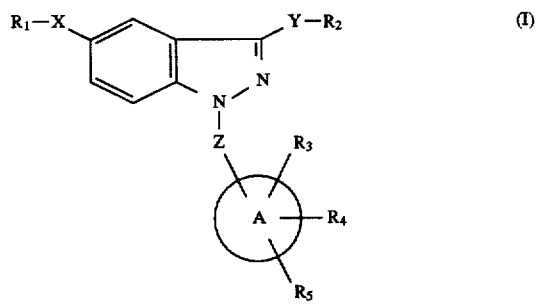

wherein
R1 is
(a) H,
(b) a $C_{1-6}$ straight or branched alkyl residue, unsubstituted, mono- or polysubstituted by
  (i) a hydroxyl residue,
  (ii) a $C_{1-6}$ alkoxy residue,
  (iii) a phenyl, naphthyl, anthranyl, or fluorenyl residue optionally substituted by a halogen atom, a nitro, or a straight or branched $C_{1-4}$ alkoxy residue,
  (iv) a phenyloxy, naphthyloxy, anthranyloxy, or fluorenyloxy residue optionally substituted by a halogen atom, nitro, or straight or branched $C_{1-4}$ alkoxy residue,
  (v) a quinolin-2-yl, or pyridine-2-yl residue,
  (vi) an amino residue,
  (vii) a —CN residue, or
  (viii) a halogen atom,
(c) a $C_{3-7}$ cycloalkyl residue,
(d) an unsubstituted phenyl, naphthyl, anthranyl, or fluorenyl residue optionally monosubstituted, or disubstituted by a halogen atom, a nitro, a straight or branched $C_{1-4}$ alkylcarboxylic, a straight or branched $C_{1-8}$ alkyl or alkoxy, a hydroxyl, a $C_{1-6}$ thioether, a straight or branched $C_{1-6}$ alkanoyl, or a benzyl residue, or
(e) a quinolin-2-ylmethoxy, or pyridin-2-ylmethoxy residue;

X is O, or a —NH, —NH—(C=O)—NH—, —NH—(C=O)—O—, —NH—(C=O)—, or —NH—CH$_2$—(C=O)— residue, wherein the last three groups are joined to the aromatic ring through the N-atom;

Y is O, or S;

R$_2$ is H;

Z is a SO, SO$_2$, —(CH$_2$)$_p$—, —(CH$_2$)$_p$—O—, —O—(CH$_2$)$_p$—, —(CH$_2$)$_p$—(C=O)—, —(C=O)—(CH$_2$)$_p$—, —(CH$_2$)$_p$—(C=O)—NH—, —NH—(C=O)—(CH$_2$)$_p$—, —(CH$_2$)$_p$—CHOH—, —CHOH—(CH$_2$)$_p$—, —(CH$_2$)$_p$—CH=CH—, or —CH=CH—(CH$_2$)$_p$— residue, wherein p is a cardinal number between 1 and 6;

A is a phenyl, naphthyl, anthranyl, fluorenyl, thiophenyl, pyridinyl, isoxazolyl, benzimidazolyl, benz[1,3]dioxolyl, pyrimidyl, pyrimidine-2,4-dionyl, quinolinyl, quinoxazolinyl, morpholinyl, or pyrrolidinyl residue; and R$_3$, R$_4$, and R$_5$ are the same or different, being (a) H;

(b) an unsubstituted straight or branched C$_{1-6}$ alkyl residue, optionally monosubstituted, or polysubstituted with
  (i) a hydroxyl residue,
  (ii) a straight or branched C$_{1-8}$ alkoxy residue,
  (iii) a phenyl, naphthyl, anthranyl, or fluorenyl residue, optionally substituted with a halogen atom, a nitro, or straight or branched C$_{1-4}$ alkoxy,
  (iv) a phenyloxy, napthyloxy, anthranyloxy, or fluorenyloxy residue, said last four residues being optionally substituted with a halogen atom, a nitro, a straight or branched C$_{1-4}$ alkoxy,
  (v) a quinolin-2-ylmethoxy, or a pyridin-2-ylmethoxy residue,
  (vi) an amino residue optionally substituted with a straight or branched C$_{1-4}$ naphthyl, anthranyl, fluorenyl, straight or branched C$_{1-4}$ alkyl phenyl, straight or branched C$_{1-4}$ alkylnaphtyl, straight or branched C$_{1-4}$ alkylanthranyl, a straight or branched C$_{1-4}$ fluorenyl residue,
  (vii) a CN residue, or
  (ix) a halogen atom, (c) a straight or branched C$_{3-7}$ cycloalkyl residue;

(d) an unsubstituted phenyl, napthyl, anthranyl, fluorenyl, quinolin-2-methoxy, or a pyridin-2-ylmethoxy residue, or monosubstituted or disubstituted with a halogen atom, a straight or branched C$_{1-6}$ alkyl, straight or branched C$_{1-6}$ alkoxy, hydroxyl, C$_{1-6}$ thioether, C$_{1-6}$ alkanoyl, or benzyl residue;

(e) a CF$_3$ residue;

(f) a NO$_2$ residue;

(g) a COOH residue;

(h) a (CH$_2$)$_p$—COOH residue in which p is a cardinal number between 1 and 6;

(i) an SO$_2$-phenyl, SO$_2$-naphthyl, SO$_2$-anthranyl, or SO$_2$-fluorenyl residue;

(j) a hydroxyl residue;

(k) a halogen atom; or (m) R$_3$ and R$_4$ form an —O—(CH$_2$)$_n$—O— bridge wherein n is a cardinal number between 1 and 3;

and pharmaceutically acceptable salts, stereoisomers, racemates, racemic modifications, and enantiomers thereof.

For the preparation of the biocompatible salts, the compounds of formula (I) are reacted in a manner known per se with inorganic or organic acids such as hydrochloric, hydrobromic, sulfuric, phosphoric, acetic, oxalic, tartaric, citric, fumaric, maleic, lactic, gluconic, glucuronic, embonic, or succinic acid, or with a base.

The invention further relates to pharmaceutical compositions containing at least one compound of formula (I), or salts thereof with biocompatible inorganic or organic acids or bases and, optionally pharmaceutically acceptable excipients and adjuncts.

The compounds of formula (I) can be administered orally, by inhalation, parenterally, intravenously or transdermally in the free form or in the form of a salt with a biocompatible acid or base.

Particularly suitable dosage forms are for oral administration, such as coated or uncoated tablets, capsules, aerosols, powder formulations for powder inhalers, as well as plasters, solutions, ampoules, and suppositories.

The active ingredient dosage of the pharmaceutical formulations depends on the age, condition and weight of the patient and on the form of administration. As a general rule of thumb the daily dose of active substance is suitably between 0.001 and 25 mg/kg body weight, but the most suitable dosages can be determined by routine dosage ranging.

The novel compounds of formula (I) include:

Example 1 1-(4-benzyloxybenzyl)-5-methoxy-1H-indazole-3-ol;

Example 2 1-(4-chlorobenzyl)-5-methoxy-1H-indazole-3-ol;

Example 3 1-(3-chlorobenzyl)-5-methoxy-1H-indazole-3-ol;

Example 4 1-(2-chlorobenzyl)-5-methoxy-1H-indazole-3-ol;

Example 5 1-(4-fluorobenzyl)-5-methoxy-1H-indazole-3-ol;

Example 6 1-(3,4-dichlorobenzyl)-5-methoxy-1H-indazole-3-ol;

Example 7 1-(2,4-dichlorobenzyl)-5-methoxy-1H-indazole-3-ol;

Example 8 1-(2,6-dichlorobenzl)-5-methoxy-1H-indazole3-ol;

Example 9 1-(2-chloro-6-flurobenzyl)-5-methoxy-1H-indazole-3-ol;

Example 10 1-(3-chloro-2-flurobenzyl)-5-methoxy-1H-indazole-3-ol;

Example 11 1-(4-bromobenzyl)-5-methoxy-1H-indazole-3-ol;

Example 12 1-(4-trifluoromethylbenzyl)-5-methoxy-1H-indazole-3-ol;

Example 13 1-(4-chloro-2-mitrobenzyl)-5-methoxy-1H-indazole-3-ol;

Example 14 1-(2-hydroxy-4-nitrobenzyl)-5-methoxy-1H-indazole-3-ol;

Example 15 1-(5-methoxy-1-(4-methoxybenzyl)-1H-indazole-3-ol;

Example 16 1-(2,4-dimethoxybenzyl)-5-methoxy-1H-indazole-3-ol;

Example 17 1-(3,4,5-trimethoxybenzyl)-5-methoxy-1H-indazole-3-ol;

Example 18 1-(2,4-dimethylbenzyl)-5-methoxy-1H-indazole-3-ol;

Example 19 1-(4-tert-butylbenzyl)-5-methoxy-1H-indazole-3-ol;

Example 20 4-(3-hydroxy-5-methoxy-1H-indazole-1-ylmethyl)benzoic acid;

Example 21 [4-(3-hydroxy-5-methoxy-1H-indazole-1-ylmethyl)phenyl]acetic acid;

Example 22 1-biphenyl-4-ylmethyl-5-methoxy-1H-indazole-3-ol;

Example 23 5-methoxy-1-naphthalen-2-ylmethyl-1H-indazole-3-ol;

Example 24 5-methoxy-1-thiophen-2-ylmethyl-1H-indazole-3-ol;

Example 25 5-methoxy-1-pyridin-2-ylmethyl-1H-indazole-3-ol;

Example 26 5-methoxy-1-pyridin-3-ylmethyl-1H-indazole-3-ol;

Example 27 5-methoxy-1-pyridin-4-ylmethyl-1H-indazole-3-ol;

Example 28 1-(3,5-dimethylisoxazol-4-ylmethyl)-5-methoxy-1H-indazole-3-ol;

Example 29 1-(2-benzenesulfonylmethylbenzyl-5-methoxy-1H-indazole-3-ol;

Example 30 1-(1H-benzimidazol-2-ylmethyl)-5-methoxy-1H-indazole-3-ol;

Example 31 1-[6-chloro-3,4-methylenedioxy)benzyl]-5-methoxy-1H-indazole-3-ol;

Example 32 6-(3-hydroxy-5-methoxy-1H-indazole-1-ylmethyl)-1H-pyrimidine-2,4-dione;

Example 33 1-(6-chloro-4-phenylquinazolin-2-ylmethyl)-5-methoxy-1H-indazole-3-ol;

Example 34 5-methoxy-1-quinolin-2-ylmethyl-1H-indazole-3-ol;

Example 35 5-methoxy-1-(3-phenylpropyl)-1H-indazole-3-ol;

Example 36 5-methoxy-1-(3-phenylallyl)-1H-indazole-3-ol;

Example 37 5-methoxy-1-(3-phenoxyethyl)-1H-indazole-3-ol;

Example 38 5-methoxy-1-(3-phenoxypropyl)-1H-indazole-3-ol;

Example 39 3-(3-hydroxy-5-methoxyindazole-1-yl)phenyl-propan-1-one

Example 40 5-methoxy-1-[2-(4-nitrophenyl)ethyl]-1H-indazole-3-ol;

Example 41 5-methoxy-1-[2-(4-nitrophenoxy)ethyl]-1H-indazole-3-ol;

Example 42 1-(4-fluorophenyl)-4-(3-hydroxy-5-methoxy-1H-indazole-1-yl)butan-1-one;

Example 43 N-(3,4-dimethoxyphenyl)-2-(3-hydroxy-5-methoxy-1H-indazole-1-yl)acetamide;

Example 44 5-methoxy-1-(2-pyridin-2-ylethyl)-1H-indazole-3-ol hydrochloride;

Example 45 5-methoxy-1-(3-pyridin-4-ylpropyl)-1H-indazole-3-ol;

Example 46 1-[2,(2,4-dichlorophenyl)-2-hydroxyethyl]-5-methoxy-1H-indazole-3-ol;

Example 47 5-methoxy-1-[2-1-methylpyrrolidin-2-yl)ethyl]-1H-indazole-3-ol;

Example 48 5-methoxy-1-(2-morpholin-4-ylethyl)-1H-indazole-3-ol;

Example 49 5-methoxyl-1-[4-quinolin-2-ylmetoxy)benzyl]-1H-indazole-3-ol;

Example 50 5-methoxyl-1-[4-quinolin-2ylmetoxy)benzyl]-1H-indazole-3-ol-dihydrochloride;

Example 51 1-(3,4-dichlorobenzyl)-1H-indazole-3,5-diol;

Example 52 1-(2,4-dichlorobenzyl)-1H-indazole-3,5-diol;

Example 53 1-quinolin-2-ylmethyl-1H-indazole-3,5-diol

Example 54 1-(4-chlorobenzyl)-1H-indazole-3,5-diol;

Example 55 5-amino-1-(2,4-dichlorobenzyl)-1H-indazole-3-ol;

Example 56 5-amino-1-(4-chlorobenzyl)-1H-indazole-3-ol;

Example 57 5-amino-1-(3,4-dichlorobenzyl)-1H-indazole-3-ol;

Example 58 1-[1-(3,4-dichlorobenzyl)-3-hydroxy-1H-indazole-5-yl]-3-(4-methoxyphenyl)urea;

Example 59 1-[1-(4-chlorobenzyl)-3-hydroxy-1H-indazole-5-yl]-3-(4-chlorophenyl)urea;

Example 60 1-[1-(3,4-dichlorobenzyl)-3-hydroxy-1H-indazole-5-yl]-3-(4-chlorophenyl)urea;

Example 61 1-[1-(4-chlorobenzyl)-3-hydroxy-1H-indazole-5-yl]-3-(3,4-dichlorophenyl)urea;

Example 62 1-[1-(3,4-dichlorobenzyl)-3-hydroxy-1H-indazole-5-yl]-3-(3,4-dichlorophenyl)urea;

Example 63 1-[1-(4-chlorobenzyl)-3-hydroxy-1H-indazole-5-yl]-3-(4-methoxyphenyl)urea;

Example 64 1-[1-(3,4-dichlorobenzyl)-3-hydroxy-1H-indazole-5-yl]-3-(4-methoxyphenyl urea;

Example 65 1-[1-(2,4-dichlorobenzyl)-3-hydroxy-1H-indazole-5-yl]-3-(4-methoxyphenyl urea;

Example 66 1-[1-(4-chlorobenzyl)-3-hydroxy-1H-indazole-5-yl]-3-naphthalen-1-ylurea;

Example 67 1-[1-(3,4-dichlorobenzyl)-3-hydroxy-1H-indazole-5-yl]-3-naphthalen-1-ylurea;

Example 68 1-[1-(4-chlorobenzyl)-3-hydroxy-1H-indazole-5-yl]-3-cyclohexylurea;

Example 69 1-cyclohexyl-3-[1-(3,4-dichlorobenzyl)-3-hydroxy-1H-indazole-5-yl]urea;

Example 70 1-cyclohexyl-3-[1-(2,4-dichlorobenzyl)-3-hydroxy-1H-indazole-5-yl]urea;

Example 71 cyclopropanecarboxylic acid [1-(4-chlorobenzyl)-3-hydroxy1H-indazole-5yl]amide Example 72 cyclopropanecarboxylic acid [1-(2,4-dichlorobenzyl)-3-hydroxy-1H-indazole-5-yl]amide; and Example 73 1-(4-chlorobenzyl)-5-methoxy-1H-indazole-3-thiol.

(A) The compounds of formula (I) can be suitably prepared by the processes of the invention. An embodiment of the process of the invention involves reacting 5-methoxy-1H-indazole-3-ol of formula (II) in the presence of a base and optionally in the presence of diluent, with a compound of formula (III), wherein $R^3$, $R^4$, $R^5$, A and Z are the same as defined in connection with formula (I) above, and Hal is a halogen atom such as F, Cl, Br, or I, to obtain a compound of formula (IV). The compound of formula (IV) is defined by the formula (I). The following optional process steps can be employed for the further processing of the compound of formula (IV) into other suitable variant compounds also defined by formula (I). Next the compound of formula (IV) is optionally further reacted with a hydrogen halide, such as hydrogen bromide, or boron tribromide, with or without the presence of a solvent to produce a compound of formula (V). The compound of formula (V) is then optionally reacted in the presence of a base and an optional diluent, with a halogen compound $R^1$—Hal of the formula (IV) to provide a compound of formula (VII).

Reaction Scheme (1):

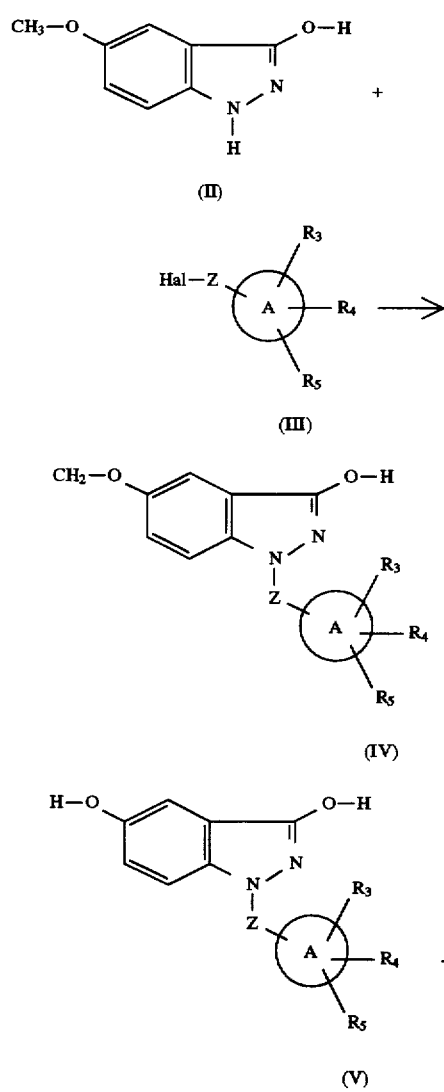

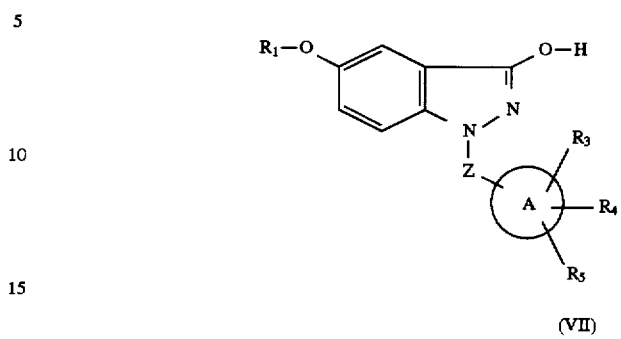

(B) According to Reaction Scheme (2) shown below, 5-nitro-1H-indazole-3-ol of Formula (VIII) is reacted, in the presence of a base and in the presence of an optional diluent, with a compound of formula (III), to provide a compound of formula (IX)⁻ which is then reduced such as with hydrogen, in the presence of a catalyst such as Raney nickel, and in the presence of a solvent, to provide a compound of formula (X), which is defined by the formula (I).

The following optional process steps can be employed for the further processing of a compound of formula (X) into other suitable variations of compounds also defined by formula (I). In this manner the compound of formula (X) can optionally be reacted with the compound of formula (XI), wherein B can be for example a halogen atom, an acid chloride group, an isocyanate group or a chlorocarbonic acid group, in the optional presence of a base and an optional diluent, to yield a compound of formula (XII).

It is also possible to convert the compound of formula (X) to a compound of the formula (V) by diazotization and boiling, and to convert a compound of formula (V) to a compound of formula (VII) as shown in Reaction Scheme 1.

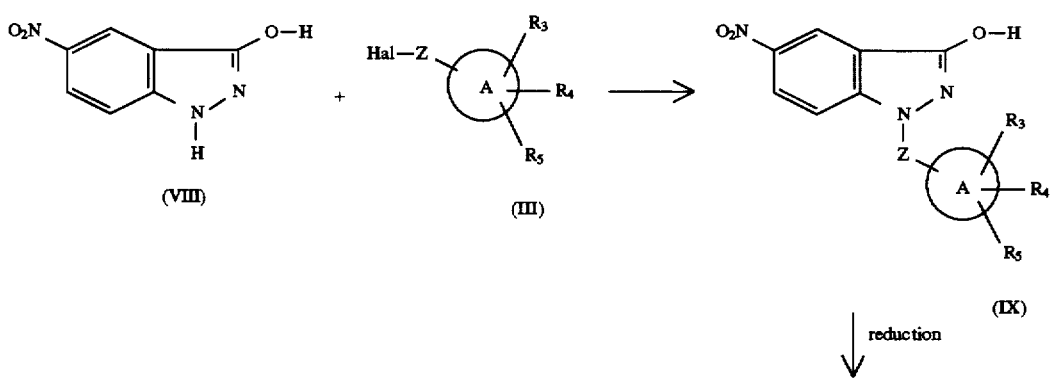

Reaction Scheme (2):

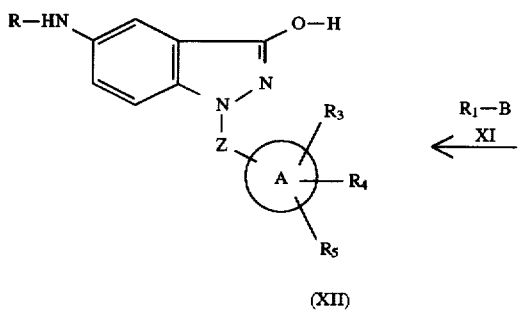

(XII)

-continued

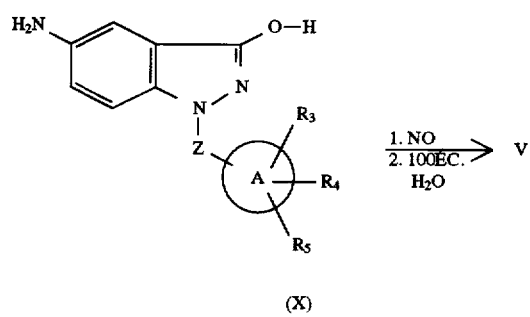

(X)

(C) According to Reaction Scheme (3) shown below, a compound of the formula (XIII), which is also encompassed among the compounds of formula (I), wherein X is O, and $R_1$ is a $C_1$-6-alkyl residue, such as a methyl, ethyl, propyl, isopropyl, butyl, isobutyl or tert-butyl, can be reacted with $P_2S_5$ (also known, as Lawesson's reagent), in the present of a solvent, to provide a compound of formula (XIV), which is also a compound of formula (I).

Reaction Scheme (3):

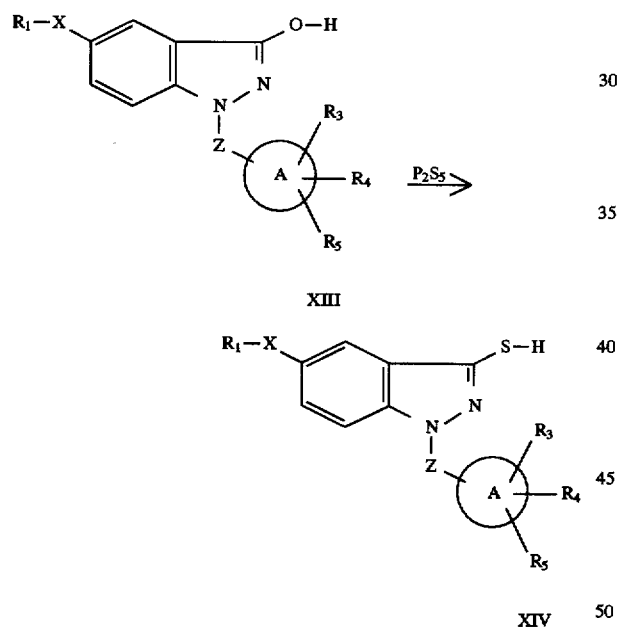

The biocompatible salts of compounds of formulae (I) or any one of (IV), (V), (VII), (X) and (XII), (XIII) and (XIV), and of Examples 1–73, can be suitably prepared by reacting them in a manner known per se with inorganic or organic acids such as hydro-chloric-, hydrobromic-, sulfuric-, phosphoric-, acetic-, oxalic-, tartaric-, citric-, fumaric-, maleic-, lactic-, gluconic-, glucuronic-, embonic-, or succinic acid, or with a base such as sodium hydroxide, potassium hydroxide, calcium hydroxide, or ammonia.

Inhibition of 5-lipoxygenase

The inhibition of arachidonate-5-lipoxygenase was determined to demonstrate antiinflammatory effect, using prepared macrophages from Wistar rats in an analogous manner known from publications, such as:

Murphy, R. C. and Matthews, W. R., Purification and Characterization of Leukotrienes from Mastocytoma Cells, Methods in Enzymology, 86, pp. 409–416.

Argentiere, D. D., Ritchie, D. M. et al., Tepoxalin: A Dual Cyclooxygenase/5-Lipoxygenase Inhibitor of Arachidonic Acid Metabolism with Potent Anti-inflammatory Activity and a Favorable Gastrointestinal Profile, The Journal of Pharmacology and Experimental Therapeutics, Vol. 271, No. 3, 1399–1408, 1994.

Carter, G. W., Young, P. R. et al., 5-Lipoxygenase Inhibitory activity of Zileuton, The Journal of Pharmacology and Experimental Therapeutics, Vol. 256, No. 3, 1991.

The experiments were all conducted as quadruple determinations, by combining four partial experiments in each case were combined to determine the mean $IC_{50}$ value. Table 1 shows the $IC_{50}$ values i.e. concentrations which cause a 50% inhibition of 5-lipoxygenase, found for the inhibition of 5-lipoxygenase by using a large and representative variety of inhibitors of a number of compounds of the Examples.

TABLE 1

| Example No. | $IC_{50}$ [nmol/l] |
|---|---|
| 1 | 171 |
| 2 | 400 |
| 3 | 470 |
| 4 | 710 |
| 6 | 410 |
| 7 | 100 |
| 8 | 750 |
| 10 | 829 |
| 11 | 765 |
| 18 | 977 |
| 19 | 696 |
| 22 | 257 |
| 23 | 265 |
| 24 | 500 |
| 31 | 874 |
| 36 | 299 |
| 37 | 745 |
| 38 | 655 |
| 39 | 150 |
| 42 | 679 |
| 49 | 86 |
| 50 | 44 |
| 51 | 748 |
| 52 | 258 |
| 61 | 278 |

As shown by the results of Table 1, the compounds of the present invention possess potent 5-lipoxygenase inhibitory properties.

Inhibition of the Antigen-induced Contraction of Tracheal Segments from Actively Sensitized Guinea-pigs The bronchodilatory action of the novel 1,3,5-trisubstituted indazole derivatives was also demonstrated in an in vitro model. For this purpose, isolated tracheal segments from guinea-pigs actively sensitized against ovalbumin by the s.c. administration of 10 µg of ovalbumin with 1 mg of aluminum hydroxide adjuvant, three weeks before removal of the organ, and a booster dose of the same amount of ovalbumin and aluminum hydroxide s.c. one week before removal of the organ. The segments were placed in organ baths filled with a nutrient solution aerated with carbogen which is a mixture of 95% oxygen and 5% carbon dioxide, and kept at 37° C., and were connected to isometric force transducers. After preincubation with mepyramine to eliminate histamine, and indomethacin for the inhibition of cyclooxygenase, $5 \times 10^{-7}$ mol/l carbachol (carbamylcholine chloride) was added and a contraction was induced. 10 µg/ml ovalbumin as an allergen was then added to the bath liquid and the maximum contraction of the tracheal segments which was thereby induced was correlated with the effect of the carbachol as control (=100%). The test substances were added to the organ bath 30 minutes before the allergen-induced contraction. Table 2 below indicates the $IC_{50}$ values, i.e. the concentrations which cause a 50% inhibition of the contraction of isolated tracheal segments from the guinea-pig. The $IC_{50}$ values were determined by testing 3–4 concentrations on 4–8 organs in each case.

TABLE 2

Inhibition of the ovalbumin-induced contraction of tracheal segments from actively sensitized guinea-pigs under mepyramine and indomethacin protection

| Example | $IC_{50}$ [µmol/l] |
|---------|--------------------|
| 1 | maximum inhibition 36% at 1.0 µmol/l |
| 6 | maximum inhibition 40% at 3.0 µmol/l |
| 50 | 2.9 µmol/l |

Slow Reacting Substance of Anaphylaxis (SRS-A) on Anaesthetized Guinea-pigs After Inhalation of Antigen The inhibition of the effect of leukotrienes in the allergic early phase can be demonstrated on sensitized guinea-pigs. For this purpose, guinea-pigs are actively sensitized against ovalbumin (OA) with 20 µg OA+20 mg Al(OH)$_3$ in 0.5 ml, administered intraperitoneally (i.p.) and a booster dose of the same is administered 14 days later. One week after the booster dose, the animals are i.p. anaesthetized with urethane and connected to an apparatus (Mumed Physiological Recorder 800) for the determination of pulmonary function parameters. The animals are pretreated with mepyramine to antagonize the histamine, with indomethacin to inhibit the formation of prostaglandins, and with propanolol to eliminate β-adrenergic mechanisms. If an allergic reaction is induced after this treatment, the associated bronchospam is extensively attributable to the effect of leukotrienes.

Before the experiment the test substances were administered orally two hours before the challenge. After an equilibration period an asthmatic challenge attack is induced by the nebulization of a 1% ovalbumin solution over 20 inspirations.

The drop in dynamic compliance is used as a suitable and well reproducible parameter for characterizing the action of leukotrienes. Under control conditions, after pretreatment and ovalbumin challenge, guinea-pigs react with a slow drop in compliance of c. 30–40% over 15 minutes. Effective inhibition of 5-lipoxygenase and hence of leukotriene formation reduces this reaction.

The results are presented in Table 3.

TABLE 3

Effect on the SRS-A bronchoconstriction in guinea-pigs sensitized with ovalbumin (OA), and on the subsequent OA challenge with 1% OA, 20 inspirations.

| Example No. | Administration | % drop in dyn. compliance | % inhibition |
|-------------|----------------|---------------------------|--------------|
| Tylose control | | | |
| 0.5% | oral, –2 hrs | 40 ± 5.7 | 0 |
| 1.0 ml/kg | | | |
| 1 | | | |
| 5.0 mg/kg | oral, –2 hrs | 32 ± 13 | 20 |
| 10.0 mg/kg | oral, –2 hrs | 9.3 ± 11 | 77 |
| 6 | | | |
| 5.0 mg/kg | oral, –2 hrs | 25 ± 9.9 | 38 |
| 10.0 mg/kg | oral, –2 hrs | 7.0 ± 2.7 | 83 |
| 50 | | | |
| 5.0 mg/kg | oral, –2 hrs | 22 ± 10 | 45 |
| 10.0 mg/kg | oral, –2 hrs | 12 ± 11 | 70 |

Inhibition of Late Phase Eosinophilia 24 Hours After the Inhalational Ovalbumin Challenge on Actively Sensitized Guinea-pigs Eosinophilic granulocytes play an important part in the transition of allergic diseases, e.g. bronchial asthma, to the chronic stage. Thus the bronchoalveolar lavage fluid (BAL) contains an increased number of eosinophils a few hours after an allergen-induced asthmatic attack. Eosinophils are expected to play an important part in cell damage since they contain histotoxic proteins, like major basic protein (MBP) and eosinophil cation protein (ECP), in their granula. It is also assumed that substances which prevent the infiltration of eosinophils have a therapeutic action against allergic diseases like bronchial asthma.

The inhibition of eosinophil infiltration by the substances was tested in vivo on guinea-pigs actively sensitized against ovalbumin by the substantenous administration of 10 µg of OA, with 1 µg of aluminum hydroxide adjuvant, three weeks before the beginning of the experiment, and a booster dose containing the same amount of OA and aluminum hydroxide was administrated substantaneously one week before the beginning of the experiment. Three weeks after the first sensitization, the animals were placed in a plastic box and exposed to an aerosol of 0.5% OA dissolved in a physiological saline solution. The nebulization time was 20–30 seconds. After 24 hours the animals were intraperitoneally anaesthetized with 1.5 g/kg body weight ethylurethane and a bronchioalveolar lavage was performed with 2×5 ml of physiological saline solution. The lavage fluid was collected and centrifuged at 400 G for 10 minutes and the cell pellet was then resuspended in 1 ml of physiological saline solution. The eosinophils were microscopically counted in a Neubauer chamber after staining using the No. 5877 Becton-Dickinson test kit for eosinophilia. The number of eosinophils was indicated in millions per animal. Each test was also carried out with two control groups with and without antigen challenge.

The percentage inhibition of the eosinophilia in the experimental groups treated with the substance is calculated by the following formula:

$$(A-C)-(B-C)/(A-C)\times 100 = \% \text{ inhibition}$$

The test substances were administered orally or intraperitoneally as a triturate in 0.5% 5-hydroxyethylcellulose two hours before the antigen challenge. The number of animals per control group and experimental group was from 8 to 17, with the results shown in Table 4.

TABLE 4

Inhibition of late phase eosinophilia 24 hours after the inhalational ovalbumin challenge on actively sensitized guinea-pigs

| Ex. | Dose [mg/kg] | Administration | EOS mill./animal $\bar{x} \pm s$ A | B | C | % inhibition |
|---|---|---|---|---|---|---|
| 1 | 1 | i.p. −2 h | 5.2 ± 2.3 | 3.3 ± 1.6 | 1.3 ± 0.55 | 48.7 |
|   | 30 | p.o. −2 h | 5.4 ± 2.9 | 3.7 ± 1.7 | 0.79 ± 0.28 | 36.0 |
| 6 | 1 | i.p. −2 h | 5.2 ± 2.3 | 2.9 ± 1.2 | 1.3 ± 0.55 | 58.8 |
|   | 30 | p.o. −2 h | 5.4 ± 2.9 | 3.5 ± 1.7 | 0.79 ± 0.29 | 40.4 |
| 50 | 10 | i.p. −2 h | 6.5 ± 2.96 | 3.8 ± 2.8 | 0.65 ± 0.35 | 46.0 |
|   | 30 | p.o. −2 h | 8.4 ± 4.0 | 6.0 ± 3.4 | 1.1 ± 0.5 | 34.0 | wherein
A is eosinophils in the control group, with challenge,
B is eosinophils in the group treated with the substance, with challenge,
C is eosinophils in the control group, without challenge, and
$\bar{X}$ is mean, and S is standard deviation

EXAMPLES

The compounds were characterized by means of melting point, thin layer chromatography, elemental analysis, NMR spectroscopy and IR and UV/VIS spectroscopy. The indazoles of formula (II) required as starting materials were prepared as described by Baiocchi et al., in Synthesis 9, 1978, 633–648.

Some of the alkylaryl halogen compounds of formula (III) are commercially available compounds or they can be obtained according by methods known per se such as from aralkyl alcohols and thionyl chloride.

The compounds of formula (VI) were prepared according to Baiocchi et al., Synthesis 9, 1978, 633–648. The preparations of some of the compounds are now given by way of example.

Example 1

1-(4-Benzyloxbenzyl)-5-methoxy-1H-indazole-3-01

3 g 5-methoxy-1H-indazole-3-01 and 4 g of 4-benzyloxybenzyl chloride are stirred in 20 ml sodium hydroxide solution for 2.5 hours at 70° C. The viscous precipitate is filtered off under suction, dissolved in 60 ml of N,N-dimethylformamide and purified by column chromatography with a 95/5 mixture of methylene chloride in methanol. The fraction containing the target product is distilled to dryness under vacuum and the residue is crystallized from acetonitrile. The precipitate is filtered off with suction and recrystallized from acetonitrile with the addition of activated charcoal.

Yield: 1.0 g. M.p.: 177.5°–179° C.

$C_{22}H_{20}N_2O_3$ (360.42), calc.: C 73.32% H 5.59% N 7.77%, found: C 73.51% H 5.75% N 7.77%

The following Examples of compounds of formula (I) of the present invention were prepared in an analogous manner, as shown below.

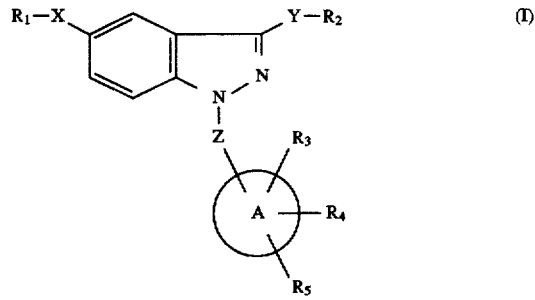

(I)

The compounds of the following Examples of the invention had the properties set out below:

| Example | X | $R_1$ | Y | $R_2$ | Z |  | $R_3, R_4, R_5$ |
|---|---|---|---|---|---|---|---|
| 2 | O | $CH_3$ | O | H | $CH_2$ |  | 4-chlorophenyl |
| 3 | " | " | " | " | " |  | 3-chlorophenyl |
| 4 | " | " | " | " | " |  | 2-chlorophenyl |
| 5 | " | " | " | " | " |  | 4-fluorophenyl |
| 6 | " | " | " | " | " |  | 3,4-dichlorophenyl |
| 7 | " | " | " | " | " |  | 2,4-dichlorophenyl |
| 8 | " | " | " | " | " |  | 2,6-dichlorophenyl |
| 9 | " | " | " | " | " |  | 2-chloro-6-fluorophenyl |
| 10 | " | " | " | " | " |  | 3-chloro-2-fluorophenyl |
| 11 | " | " | " | " | " |  | 4-bromophenyl |
| 12 | " | " | " | " | " |  | 4-trifluromethylphenyl |
| 13 | " | " | " | " | " |  | 4-chloro-2-nitrophenyl |
| 14 | " | " | " | " | " |  | 2-hydroxy-4-nitrophenyl |
| 15 | " | " | " | " | " |  | 4-methoxyphenyl |
| 16 | " | " | " | " | " |  | 2,4-dimethoxyphenyl |
| 17 | " | " | " | " | " |  | 3,4,5-trimethoxyphenyl |
| 18 | " | " | " | " | " |  | 3,4-dimethylphenyl |
| 19 | " | " | " | " | " |  | 4-tert-butylphenyl |
| 20 | " | " | " | " | " |  | 4-benzoic acid |

-continued

| Example | X | R₁ | Y | R₂ | Z | 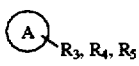 R₃, R₄, R₅ |
|---|---|---|---|---|---|---|
| 21 | " | " | " | " | " | 4-phenylacetic acid |
| 22 | " | " | " | " | " | biphenyl-4-yl |
| 23 | " | " | " | " | " | naphth-2-yl |
| 24 | " | " | " | " | " | thiophen-2-yl |
| 25 | " | " | " | " | " | pyridin-2-yl |
| 26 | " | " | " | " | " | pyridin-3-yl |
| 27 | " | " | " | " | " | pyridin-4-yl |
| 28 | " | " | " | " | " | 3,5-dimethylisoxazole |
| 29 | " | " | " | " | " | 2-benzenesulphonyl-methylphenyl |
| 30 | " | " | " | " | " | 1H-benzimidazol-2-yl |
| 31 | " | " | " | " | " | 6-chloro-3,4-(methylene-dioxy)phenyl |
| 32 | " | " | " | " | " | 1H-pyrimidin-2,4-dion-6-yl |
| 33 | " | " | " | " | " | 6-(chloro-4-phenylquinazolin-2-yl) |
| 34 | " | " | " | " | " | quinolin-2-yl |
| 35 | " | " | " | " | (CH₂)₃— | phenyl |
| 36 | " | " | " | " | CH₂—CH=CH— | " |
| 37 | " | " | " | " | (CH₂)₂—O— | " |
| 38 | " | " | " | " | (CH₂)₃—O— | " |
| 39 | " | " | " | " | (CH₂)₂—C=O | " |
| 40 | " | " | " | " | (CH₂)₂— | 4-nitrophenyl |
| 41 | " | " | " | " | (CH₂)₂—O— | " |
| 42 | " | " | " | " | (CH₂)₃—C=O | 4-fluorophenyl |
| 43 | " | " | " | " | CH₂—CONH— | 3,4-dimethoxyphenyl |
| 44 | " | " | " | " | (CH₂)₂— | pyridin-2-yl × HCl |
| 45 | " | " | " | " | (CH₂)₃— | pyridin-4-yl |
| 46 | " | " | " | " | CH₂—CH(OH)— | 2,4-dichlorophenyl |
| 47 | " | " | " | " | (CH₂)₂— | 1-methylpyrrolidin-2-yl |
| 48 | " | " | " | " | " | 2-morpholin-4-yl |

The properties of the compounds of the following Examples of the invention had the properties set out below:

| Example | Empirical formula | M.p. [°C.] | Molecular weight | C calc. | H calc. | N calc. | C found | H found | N found |
|---|---|---|---|---|---|---|---|---|---|
| 2 | $C_{15}H_{13}ClN_2O_2$ | 194–196 | 288.74 | 62.40 | 4.54 | 9.70 | 60.02 | 4.55 | 9.35 |
| 3 | $C_{15}H_{13}ClN_2O_2$ | 167–168 | 288.74 | 62.40 | 4.57 | 9.70 | 62.17 | 4.38 | 9.55 |
| 4 | $C_{15}H_{13}ClN_2O_2$ | 190–191 | 288.74 | 62.40 | 4.57 | 9.70 | 62.45 | 5.53 | 9.74 |
| 5 | $C_{15}H_{13}FN_2O_2$ | 202–204 | 272.28 | 66.17 | 4.91 | 10.29 | 63.57 | 4.74 | 9.92 |
| 6 | $C_{15}H_{12}Cl_2N_2O_2$ | 194–195 | 323.18 | 55.75 | 3.74 | 8.67 | 55.85 | 3.68 | 8.63 |
| 7 | $C_{15}H_{12}Cl_2N_2O_2$ | 214–215 | 323.18 | 55.75 | 3.74 | 8.67 | 55.69 | 3.75 | 8.62 |
| 8 | $C_{15}H_{12}Cl_2N_2O_2$ | 214–215 | 323.18 | 55.75 | 3.74 | 8.67 | 55.11 | 3.73 | 8.51 |
| 9 | $C_{15}H_{12}ClFN_2O_2$ | 189 | 306.73 | 58.74 | 3.94 | 9.13 | 59.80 | 3.91 | 9.10 |
| 10 | $C_{15}H_{12}ClFN_2O_2$ | 194–195 | 306.73 | 55.74 | 3.94 | 9.13 | 58.28 | 3.82 | 8.95 |
| 11 | $C_{15}H_{13}BrN_2O_2$ | 189 | 333.19 | 54.07 | 3.93 | 8.41 | 54.06 | 3.93 | 8.35 |
| 12 | $C_{16}H_{13}F_3N_2O_2$ | 165–167 | 322.29 | 59.63 | 4.07 | 8.69 | 59.26 | 3.94 | 8.50 |
| 13 | $C_{15}H_{12}ClN_3O_4$ | 212–215 | 333.73 | 53.98 | 3.63 | 12.59 | 54.04 | 3.66 | 12.69 |
| 14 | $C_{15}H_{13}N_3O_5$ | 224 | 315.29 | 57.14 | 4.15 | 13.33 | 57.27 | 4.12 | 13.38 |
| 16 | $C_{17}H_{18}N_2O_4$ | 151–154 | 314.34 | 64.96 | 5.77 | 8.91 | 64.91 | 5.69 | 9.01 |
| 17 | $C_{18}H_{20}N_2O_5$ | 180 | 344.37 | 62.78 | 5.85 | 8.13 | 62.58 | 5.83 | 8.08 |
| 18 | $C_{17}H_{18}N_2O_2$ | 209–219 | 282.35 | 72.32 | 6.43 | 9.92 | 72.36 | 6.53 | 9.82 |
| 19 | $C_{19}H_{22}N_2O_2$ | 202–205 | 310.40 | 73.52 | 7.14 | 9.02 | 73.36 | 7.15 | 8.93 |
| 20 | $C_{16}H_{14}N_2O_4$ | 220–223 | 298.30 | 64.42 | 4.73 | 9.39 | 64.26 | 4.70 | 9.14 |
| 21 | $C_{17}H_{16}N_2O_4$ | 192–196 | 312.33 | 65.37 | 5.16 | 8.97 | 65.31 | 5.25 | 9.01 |
| 22 | $C_{21}H_{18}N_2O_2$ | 214–218 | 330.39 | 76.34 | 5.49 | 8.48 | 76.33 | 5.50 | 8.38 |
| 23 | $C_{19}H_{16}N_2O_2$ | 187–194 | 304.35 | 74.98 | 5.30 | 9.21 | 74.57 | 5.18 | 9.24 |
| 24 | $C_{13}H_{12}N_2O_2S$ | 186 | 260.32 | 59.98 | 4.65 | 10.76 | 59.61 | 4.72 | 10.63 |
| 25 | $C_{14}H_{13}N_3O_2$ | 166–167 | 255.28 | 65.87 | 5.13 | 16.46 | 65.26 | 5.21 | 16.26 |
| 26 | $C_{14}H_{13}N_3O_2$ | 153 | 255.28 | 65.87 | 5.13 | 16.46 | 65.45 | 5.11 | 16.43 |
| 27 | $C_{14}H_{13}N_3O_2$ | 150 | 255.28 | 65.87 | 5.13 | 16.46 | 65.18 | 5.00 | 16.35 |
| 28 | $C_{14}H_{13}N_3O_3$ | 195 | 273.29 | 61.53 | 5.53 | 15.37 | 61.60 | 5.63 | 15.55 |
| 29 | $C_{22}H_{20}N_2O_4S$ | 219–221 | 408.48 | 64.69 | 4.94 | 6.86 | 64.70 | 4.92 | 6.61 |
| 30 | $C_{16}H_{14}N_4O_2$ | 210–214 | 294.32 | 65.29 | 4.79 | 19.04 | 65.11 | 4.80 | 18.96 |
| 31 | $C_{16}H_{13}ClN_2O_4$ | 227–229 | 332.75 | 57.75 | 3.94 | 8.42 | 57.66 | 3.91 | 8.52 |
| 32 | $C_{14}H_{16}N_4O_5$ | >330 | 320.31 | 52.49 | 5.03 | 17.49 | 52.63 | 4.24 | 17.41 |
| 33 | $C_{22}H_{17}ClN_4O_2 \times 2H_2O$ | 218–222 | 452.90 | 60.99 | 4.67 | 12.37 | 60.66 | 4.55 | 11.42 |
| 34 | $C_{18}H_{15}N_3O_2$ | 179–194 | 305.34 | 70.80 | 4.95 | 13.76 | | | |

-continued

| Ex-ample | Empirical formula | M.p. [°C.] | Molecular weight | Elemental analysis [%] calc. / found | | |
|---|---|---|---|---|---|---|
| | | | | C | H | N |
| 35 | $C_{17}H_{18}N_2O_2$ | 160 | 282.34 | 70.57 / 72.32 | 4.95 / 6.43 | 13.76 / 9.92 |
| | | | | 71.82 | 6.52 | 9.76 |
| 36 | $C_{17}H_{16}N_2O_2$ | 183–187 | 280.33 | 72.84 / 72.94 | 5.75 / 5.78 | 9.99 / 9.92 |
| 37 | $C_{16}H_{16}N_2O_3$ | 165–175 | 284.32 | 67.59 / 67.19 | 5.67 / 5.66 | 9.85 / 9.64 |
| 39 | $C_{17}H_{18}N_2O_3$ | 136–142 | 298.34 | 68.44 / 68.67 | 6.08 / 6.17 | 9.39 / 9.21 |
| 39 | $C_{17}H_{16}N_2O_3$ | 171–172 | 296.33 | 68.90 / 69.04 | 5.44 / 5.53 | 9.46 / 9.47 |
| 40 | $C_{16}H_{15}N_3O_4$ | 239–240 | 313.32 | 61.33 / 61.07 | 4.83 / 4.82 | 13.41 / 13.41 |
| 41 | $C_{14}H_{15}O_5N_3 \times \frac{1}{4}H_2O$ | 205–210 | 333.82 | 57.56 / 57.51 | 4.68 / 4.63 | 12.59 / 11.91 |
| 42 | $C_{18}H_{17}FN_2O_3$ | 163–165 | 328.35 | 65.84 / 65.69 | 5.22 / 5.21 | 8.53 / 8.56 |
| 43 | $C_{18}H_{19}N_3O_5$ | 225–233 | 357.37 | 60.49 / 60.13 | 5.36 / 5.34 | 11.76 / 11.84 |
| 44 | $C_{15}H_{17}Cl_2N_3O_2$ | 143–145 | 342.23 | 52.64 / 52.36 | 5.01 / 5.06 | 12.28 / 12.05 |
| 45 | $C_{16}H_{17}N_3O_2$ | 171 | 283.33 | 67.83 / 67.78 | 6.05 / 6.06 | 14.83 / 14.80 |

Example 49

1-[4-Quinolin-2-ylmethoxy benzyl-5-methoxy-1H-indazole-3-ol 3.6 g 5-methoxy-11H-indazole-3-ol, 6.4 g 2-(4-chloromethyl phyenoxymethyl) quinoline hydrochloride and 2.4 g sodium hydroxide are stirred in 60 ml dimethyl sulfoxide for six hours at 20°–30° C. The mixture is then extracted with 200 ml of chloroform and 400 ml water. The aqueous phase is re-extracted by shaking with 100 ml chloroform and the combined chloroform phases are washed three times with 400 ml water, dried over sodium sulphate and distilled to dryness. The residue is crystallized from a small amount of ethyl acetate, filtered off with suction and recrystallized from ethyl acetate with the addition of activated charcoal.

Yield: 0.6 g M.p.: 165.5°–169° C.

$C_{25}H_{21}N_3O_3$ (411.46) calc.: C 72.79% H 5.38% N 10.19%, found: C 72.82% H 5.15% N 10.21%

Example 50

1-[4-Quinolin-2-ylmethoxy)benzyl]-5-methoxy-1H-indazole-3-ol dihydrochloride 1.2 g 1-[4-quinolin-2-ylmethoxy)benzyl]-5-methoxy-1H-indazole-3-ol of Example 49 are dissolved in 200 ml acetone, and 0.8 ml of a solution 7.03 mol/l hydrogen chloride in 2-propanol is added, while stirring. The mixture is then stirred for one hour at room temperature, and for 30 minutes at 0° C. The precipitate is filtered off with suction, washed with acetone and dried.

Yield: 1.2 g M.p.: 174.5°–181° C.

$C_{25}H_{21}N_3O_3 \times 2HCl$ (484.39), calc.: C 61.94% H 4.79% N 8.68% Cl 14.64, found: C 61.99% H 4.71% N 8.74% Cl 14.17

The 1-substituted 3,5-dihydroxy-1H-indazoles of formula (V) are prepared by the ether cleavage of a 5-alkoxy derivative or by the diazotization and boiling of a 5-amino derivative according to Reaction Scheme (2).

Example 51

1-(3,4-Dichlorobenzyl)-1H-indazole-3,5-diol 4.85 g 1-(3,4-dichlorobenzyl)-5-methoxy-1H-indazole-3-ol are heated in 30 ml acetic acid and 30 ml 50% hydrobromic acid for 4 hours under gentle reflux. After cooling, the mixture is stirred into 250 ml water, rendered alkaline with concentrated sodium hydroxide solution and extracted twice with 80 ml tert-butyl methyl ether. The aqueous phase is acidified with sulfuric acid and extracted by shaking three times with 200 ml tert-butyl methyl ether. The combined ether phases are dried over sodium sulfate and distilled to dryness under vacuum. The residue is washed with a small amount of tert-butyl methyl ether and dried.

Yield: 2.4 g M.p.: 239°–243.5° C.

$C_{14}H_{10}Cl_2N_2O_2$ (309.15), calc.: C 54.38% H 3.26% N 9.06%, found: C 54.12% H 3.29% N 9.03%

The following Examples were prepared analogously to the foregoing.

| Example | X | $R_1$ | Y | $R_2$ | Z | A, $R_3$, $R_4$, $R_5$ |
|---|---|---|---|---|---|---|
| 52 | O | H | O | H | $CH_2$ | 2,4-dichlorophenyl |
| 53 | " | " | " | " | " | quinolin-2-yl |

| Ex-ample | Empirical formula | M.p. [°C.] | Molecular weight | Elemental analysis [%] calc. / found | | |
|---|---|---|---|---|---|---|
| | | | | C | H | N |
| 52 | $C_{14}H_{10}Cl_2N_2O_2$ | 216–225 | 309.15 | 54.38 / 54.17 | 3.26 / 3.28 | 9.06 / 9.02 |
| 53 | $C_{17}H_{13}N_3O_2 \times 0.5 H_2O$ | 140–150 | 300.31 | 67.99 / 67.97 | 4.70 / 4.69 | 13.99 / 13.28 |

Example 54

1-(Chlorobenzyl-1H-indazole-3,5-diol

A solution of 1.26 g sodium nitrite in 5 ml water is added dropwise at 0° C. to a solution of 2 g 5-amino-1-(4-chlorobenzyl)-1H-indazole-3-ol in 180 ml n-butanol and 20 ml 3.3N sodium hydroxide solution. After stirring for one hour at 0°–5° C., the mixture is stirred for one hour at 80° C. After cooling, it is distilled to dryness under vacuum. The residue is partitioned between 100 ml water and 200 ml tert-butyl methyl ether, and the ether layer is re-extracted by shaking with 100 ml water. The ether layer is dried over sodium sulfate, distilled to dryness and dried under vacuum.

Yield: 3.0 g, M.p.: resin $^{13}$C NMR (DMSO-$d_6$; 300 MHz): δ50.96; 110.98; 112.65; 115.27; 123.07; 128.53; 129.55; 132.41; 137.01; 140.46; 154.89

The known starting compounds of formula (VIII) were prepared as described by Pfannstiel et al., in Ber. Dtsch. Chem. Ges. 75 (9), 1096–1107 (1942).

The known compounds of formula (IX) were synthesized according to Aran et al., in JU. Chem. Soc. Perkin Trans. I, 1993, 1119–1127, and Baiocchi et al., Synthesis 1978 (9), 633–648.

Example 55

5-Amino-1-(2,4-dicloroben1)-1H-indazole-3-ol 14.4 g 5-nitro-1H-indazole-3-ol and 15.64 g 2,4-dichlorobenzyl chloride are stirred in 80 ml 1N sodium hydroxide solution for four hours at 70° C. A further 5.54 g 2,4-dichlorobenzyl chloride and 20 ml 1N sodium hydroxide solution are added and the mixture is stirred for 2.5 hours at 70° C. After cooling, the product is filtered off under suction and recrystallized from n-butanol with the addition of activated charcoal.

Yield: 25.0 g 16.2 g of the resulting 1-(2,4-dichlorobenzyl)-5-nitro-1H-indazole-3-ol are hydrogenated with hydrogen for 6 hours at 20 bar and 100° C., in the presence of 5 g Raney nickel and 800 ml dioxane. After filtration of the catalyst with suction, the filtrate is concentrated to dryness under vacuum. The residue is recrystallized from n-butanol with the addition of activated charcoal.

Yield: 8.7 g M.p.: 199°–202.5° C.

$C_{14}H_{11}Cl_2N_3O$ (308.17), calc.: C 54.56% H 3.60% N 13.64%, found: C 54.72% H 3.73% N 13.56%

The following Examples were prepared analogously to the foregoing:

| Example | X | $R_1$ | Y | $R_2$ | Z | (A) $R_3, R_4, R_5$ |
|---|---|---|---|---|---|---|
| 56 | NH | H | O | H | CH | 4-chlorophenyl |
| 57 | " | " | " | " | " | 3,4-dichlorophenyl |

| Example | Empirical formula | M.p. [°C.] | Molecular weight | calc. found | C C | H H | N N |
|---|---|---|---|---|---|---|---|
| 56 | $C_{14}H_{12}ClN_3O$ | 200–208 | 273.72 | | 61.43 61.53 | 4.42 4.42 | 15.35 15.48 |
| 57 | $C_{14}H_{11}Cl_2N_3O$ | 215–220 | 308.17 | | 54.56 54.89 | 3.60 3.71 | 13.64 13.63 |

The reaction of the 5-amino derivatives X with compounds of formula (XI) having the formula $R_1$—B is carried out for example, as follows:

Example 58

1-[1-(3,4-Dichlorobenzyl)-3-hydroxy-1H-indazole-5-yl]-3-(4-methoxyphenyl) urea 1.54 g 5-amino-1-(3,4-dichlorobenzyl)-1H-indazole-3-ol and 1.12 g 4-methoxyphenyl isocyanate are stirred in 75 ml tetrahydrofuran for 5 hours at room temperature. the solution is concentrated to one third of its volume under vacuum and the precipitate crystallized out after cooling is filtered off under suction. It is recrystallized from n-butanol.

Yield: 1.55 g, M.p.: 267°–276° C.

Examples 59 to 70 were prepared analogously to these methods. For the synthesis of Examples 71 and 72 the isocyanate was replaced with cyclopropanyl chloride.

| Example | X | $R_1$ | Y | $R_2$ | Z | (A) $R_3, R_4, R_5$ |
|---|---|---|---|---|---|---|
| 59 | NH | Cl—⟨phenyl⟩—NHCO | O | H | $CH_2$ | 4-chlorophenyl |
| 60 | " | " | " | " | " | 3,4-dichlorophenyl |
| 61 | " | Cl,Cl—⟨phenyl⟩—NHCO | " | " | " | 4-chlorophenyl |
| 62 | " | " | " | " | " | 3,4-dichlorophenyl |
| 63 | " | $CH_3O$—⟨phenyl⟩—NHCO | " | " | " | 4-chlorophenyl |
| 64 | " | " | " | " | " | 3,4-dichlorophenyl |
| 65 | " | " | " | " | " | 2,4-dichlorophenyl |
| 66 | NH | ⟨naphthyl⟩—NHCO | O | H | $CH_2$ | 4-chlorophenyl |
| 67 | " | " | " | " | " | 3,4-dichlorophenyl |
| 68 | " | ⟨cyclohexyl⟩—NHCO | " | " | " | 4-chlorophenyl |

-continued

| | | | | | | |
|---|---|---|---|---|---|---|
| 69 | " | " | " | " | " | 3,4-dichlorophenyl |
| 70 | " | " | " | " | " | 2,4-dichlorophenyl |
| 71 | " | ▷—CO | " | " | " | 4-chlorophenyl |
| 72 | " | " | " | " | " | 2,4-dichlorophenyl |

| Example | Empirical formula | M.p. [°C.] | Molecular weight | Elemental analysis [%] calc. / found | | |
|---|---|---|---|---|---|---|
| | | | | C | H | N |
| 59 | $C_{21}H_{16}Cl_2N_4O_2$ | 277–285 | 427.29 | 59.03 | 3.77 | 13.11 |
| | | | | 58.14 | 4.09 | 12.01 |
| 60 | $C_{21}H_{15}Cl_2N_4O_2$ | 262–273 | 461.74 | 54.62 | 3.28 | 12.13 |
| | | | | 54.84 | 3.42 | 12.24 |
| 61 | $C_{22}H_{15}ClN_4O_3$ | 282–292 | 422.87 | 62.48 | 4.53 | 13.25 |
| | | | | 62.56 | 4.57 | 13.09 |
| 62 | $C_{21}H_{14}Cl_4N_4O_2$ | 258–263 | 496.18 | 50.83 | 2.84 | 11.29 |
| | | | | 50.60 | 2.98 | 11.24 |
| 63 | $C_{22}H_{19}ClN_4O_3$ | 285–290 | 422.87 | 62.48 | 4.53 | 13.25 |
| | | | | 62.56 | 4.57 | 13.09 |
| 64 | $C_{22}H_{18}Cl_2N_4O_3$ | 267–276 | 457.32 | 57.78 | 3.92 | 12.25 |
| | | | | 57.76 | 3.98 | 12.28 |
| 65 | $C_{22}H_{18}Cl_2N_4O_3$ | 301–306 | 457.32 | 57.78 | 3.97 | 12.25 |
| | | | | 57.50 | 3.97 | 12.27 |
| 66 | $C_{25}H_{19}ClN_4O_2$ | 281–290 | 442.91 | 67.78 | 4.32 | 12.58 |
| | | | | 67.79 | 4.44 | 12.55 |
| 67 | $C_{25}H_{18}Cl_2N_4O_2$ | 255–262 | 477.35 | 62.90 | 3.80 | 11.74 |
| | | | | 62.85 | 3.84 | 11.73 |
| 68 | $C_{21}H_{23}ClN_4O_2$ | 248–250 | 398.90 | 63.22 | 5.81 | 14.05 |
| | | | | 63.14 | 5.81 | 14.13 |
| 69 | $C_{21}H_{22}Cl_2N_4O_2$ | 240–245 | 433.34 | 58.20 | 5.12 | 12.93 |
| | | | | 58.23 | 5.14 | 12.87 |
| 70 | $C_{21}H_{22}Cl_2N_4O_2$ | 308–310 | 433.34 | 58.20 | 5.12 | 12.93 |
| | | | | 58.13 | 5.14 | 12.94 |
| 72 | $C_{18}H_{15}Cl_2N_3O_2$ | 280–288 | 376.25 | 57.46 | 4.02 | 11.17 |
| | | | | 56.66 | 3.94 | 10.71 |

Compounds of formula (XIV) are synthesized according to the method described by G. Corsi and G. Palazzo, in Ann. Chim. (Rome) 60, 246–258 (1970).

Example 73

1-(4Chlorobenyl)-5-methoxy-1H-indazole-3-thiol 2.74 g 1-(4-chlorobenzyl)-5-methoxy-1H-indazole-3-ol and 1.2 g $P_2S_5$ are heated in 5 ml quinoline for 45 minutes at 185°–190° C. The solution is then poured into ice water and acidified with concentrated hydrochloric acid. The aqueous phase is extracted with 25 ml chloroform and the chloroform phase is extracted by shaking twice with 20 ml water. The chloroform phase is dried over magnesium sulfate and concentrated. The residue is purified by column chromatograph with a 10/0.05 mixture of methylene chloride with methanol.

Yield: 1.0 g, M.p.: 62°–64° C.

$C_{15}H_{13}ClN_2OS$ (304.80), calc.: C 59.11% H 4.29% N 9.19%, found: C 59.56% H 4.03% N 9.16%

We claim:

1. A 1,3,5-trisubstituted indazole derivative of the formula

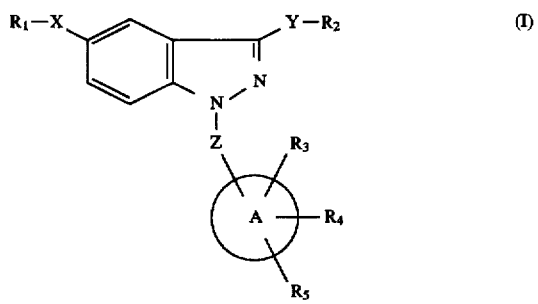

wherein
R1 is
 (a) H,
 (b) a $C_{1-6}$ straight or branched alkyl residue, unsubstituted, mono- or polysubstituted by
  (i) a hydroxyl residue,
  (ii) a $C_{1-6}$ alkoxy residue,
  (iii) a phenyl, naphthyl, anthranyl, or fluorenyl residue optionally substituted by a halogen atom, a nitro, or a straight or branched $C_{1-4}$ alkoxy residue,
  (iv) a phenyloxy, naphthyloxy, anthranyloxy, or fluorenyloxy residue optionally substituted by a halogen atom, nitro, or straight or branched $C_{1-4}$ alkoxy residue, (v) a quinolin-2-yl, or pyridine-2-yl residue,
(vi) an amino residue,
(vii) a —CN residue, or
(viii) a halogen atom,
(c) a $C_{3-7}$ cycloalkyl residue,
(d) an unsubstituted phenyl, naphthyl, anthranyl, or fluorenyl residue optionally monosubstituted, or disubstituted by a halogen atom, a nitro, a straight or branched $C_{1-4}$ alkylcarboxylic, a straight or branched $C_{1-8}$ alkyl or alkoxy, a hydroxyl, a $C_{1-6}$ thioether, a straight or branched $C_{1-6}$ alkanoyl, or a benzyl residue, or
(e) a quinolin-2-ylmethoxy, or pyridin-2-ylmethoxy residue;

X is O, or a —NH, —NH—(C=O)—NH—, —NH—(C=O)—O—, —NH—(C=O)—, or —NH—CH$_2$—(C=O)— residue, wherein the last three groups are joined to the aromatic ring through the N-atom;

Y is O, or S;

$R_2$ is H;

Z is a SO, SO$_2$, —(CH$_2$)$_p$—, —(CH$_2$)—O—, —O—(CH$_2$)$_p$—, —(CH$_2$)$_p$—(C=O)—, —(C=O)—(CH$_2$)$_p$—, —(CH$_2$)$_p$—(C=O)—NH—, —NH—(C=O)—(CH$_2$)$_p$—, —(CH$_2$)$_p$—CHOH—, —CHOH—(CH$_2$)$_p$—, —(CH$_2$)$_p$—CH=CH—, or —CH=CH—(CH$_2$)$_p$— residue, wherein p is a cardinal number between 1 and 6;

A is a phenyl, naphthyl, anthranyl, fluorenyl, thiophenyl, pyridinyl, isoxazolyl, benzimidazolyl, benz[1,3]dioxolyl, pyrimidyl, pyrimidine-2,4-dionyl, quinolinyl, quinoxazolinyl, morpholinyl, or pyrrolidinyl residue; and $R_3$, $R_4$, and $R_5$ are the same or different, being (a) H, provided that when Z is (CH$_2$)$_p$ when p=1, and A is phenyl, then $R_3$, $R_4$, and $R_5$ are not H;
(b) an unsubstituted straight or branched $C_{1-6}$ alkyl residue, optionally monosubstituted, or polysubstituted with
(i) a hydroxyl residue,
(ii) a straight or branched $C_{1-8}$ alkoxy residue,
(iii) a phenyl, naphthyl, anthranyl, or fluorenyl residue, optionally substituted with a halogen atom, a nitro, or straight or branched $C_{1-4}$ alkoxy,
(iv) aphenyloxy, napthyloxy, anthranyloxy, or fluorenyloxy residue, said last four residues being optionally substituted with a halogen atom, a nitro, a straight or branched $C_{1-4}$ alkoxy,
(v) a quinolin-2-ylmethoxy, or a pyridin-2-ylmethoxy residue,
(vi) an amino residue optionally substituted with a straight or branched $C_{1-4}$ alkyl, phenyl, naphthyl, anthranyl, fluorenyl, straight or branched $C_{1-4}$ alkylphenyl, straight or branched $C_{1-4}$ alkylnaphtyl, straight or branched $C_{1-4}$ alkylanthranyl, a straight or branched $C_{1-4}$ fluorenyl residue,
(vii) a CN residue, or
(ix) a halogen atom,
(c) a straight or branched $C_{3-7}$ cycloalkyl residue;
(d) an unsubstituted phenyl, napthyl, anthranyl, fluorenyl, quinolin-2-methoxy, or a pyridin-2-ylmethoxy residue, or monosubstituted or disubstituted with a halogen atom, a straight or branched $C_{1-6}$ alkyl, straight or branched $C_{1-6}$ alkoxy, hydroxyl, $C_{1-6}$ thioether, $C_{1-6}$ alkanoyl, or benzyl residue;

(e) a CF$_3$ residue;
(f) an NO$_2$ residue;
(g) a COOH residue;
(h) a (CH$_2$)$_p$—COOH residue in which p is a cardinal number between 1 and 6;
(i) an SO$_2$-phenyl, SO$_2$-naphtbyl, SO$_2$-anthranyl, or SO$_2$-fluorenyl residue;
(j) a hydroxyl residue;
(k) a halogen atom; or
(m) $R_3$ and $R_4$ form an —O—(CH$_2$)$_n$—O— bridge wherein n is a cardinal number between 1 and 3;

and pharmaceutically acceptable salts, stereoisomers, racemates, racemic modifications, and enantiomers thereof.

2. A compound of claim 1, which is 1-(4-benzyloxybenzyl)-5-methoxy-1H-indazol-3-ol;

1-(4-chlorobenzyl)-5-methoxy-1H-indazol-3-ol;

1-(3-chlorobenzyl)-5-methoxy-1H-indazol-3-ol;

1-(2-chlorobenzyl)-5-methoxy-1H-indazol-3-ol;

1-(4-fluorobenzyl)-5-methoxy-1H-indazol-3-ol;

1-(3,4-dichlorobenzyl)-5-methoxy-1H-indazol-3-ol;

1-(2,4-dichlorobenzyl)-5-methoxy-1H-indazol-3-ol;

1-(2,6-dichlorobenzyl)-5-methoxy-1H-indazol-3-ol;

1-(2-chloro-6-flurobenzyl)-5-methoxy-1H-indazol-3-ol;

1-(3-chloro-2-flurobenzyl)-5-methoxy-1H-indazol-3-ol;

1-(4-bromobenzyl)-5-methoxy-1H-indazol-3-ol;

1-(4-trifluoromethylbenzyl)-5-methoxy-1H-indazol-3-ol;

1-(4-chloro-2-nitrobenzyl)-5-methoxy-1H-indazol-3-ol;

1-(2-hydroxy-4-nitrobenzyl)-5-methoxy-1H-indazol-3-ol;

1-(5-methoxy-1-(4-methoxybenzyl)-1H-indazol-3-ol;

1-(2,4-dimethoxybenzyl)-5-methoy-1H-indazol-3-ol;

1-(3,4,5-trinethoxybenzyl)-5-methoxy-1H-indazol-3-ol;

1-(2,4-dimethylbenzy)-5-methoxy-1H-indazol-3-ol;

1-(4tert-butylbenzyl)-5-methoxy-1H-indazol-3-ol;

4-(3-hydroxy-5-methoxy-1H-indazol-1-yl-methyl) benzoic acid;

[4(3-hydroxy-5-methoxy-1H-indazol-1-yl-methyl) phenyl]acetic acid;

1-biphenyl-4-ylmethyl-5-methoxy-1H-indazol-3-ol;

5-mnethoxy-1-naphthalen-2-ylmethyl-1H-indazol-3-ol;

5-methoxy-1-thiophen-2-ylmethyl-1H-indazol-3-ol;

5-methoxy-1-pyridin-2-ylmethyl-1H-indazol-3-ol;

5-methoxy-1-pyridin-3-ylmethyl-1H-indazol-3-ol;

5-methoxy-1-pyridin-4-ylmethyl-1H-indazol-3-ol;

1-(3,5-dimethylisoxazol-4-ylmethyl)-5-methoxy-1H-indazol-3-ol;

1-(2-benzenesulthonylmethylbenzyl-5-methoxy-1H-indazol-3-ol;

1-(1H-benzimidazol-2-ylmethyl)-5-methoxy-1H-indazol-3-ol;

1-[6-chloro-3,4-methylenedioxy)benzyl]-5-methoxy-1H-indazol-3-ol;

6-(3-hydroxy-5-methoxy-1H-indazol-1-yl-methyl)-1H-pyrimidine-2,4-dione;

1-(6-chloro-4-phenylquinazolin-2-ylmethyl)-5-methoxy-1H-indazol-3-ol;

5-methoxy-1-quinolin-2-ylmethyl-1H-indazol-3-ol;

5-methoxy-1-(3-phenylpropyl)-1H-indazol-3-ol;

5-methoxy-1-(3-phenylallyl)-1H-indazol-3-ol;

5-methoxy-1-(3-phenoxyethyl)-1H-indazol-3-ol;

5-methoxy-1-(3-phenoxypropyl)-1H-indazol-3-ol;

3-(3-hydroxy-5-methoxyindazol-1-yl)phenyl-propan-1-one 5-methoxy-1-[2-(4-nitrophenyl)ethyl]-1H-indazol-3-ol;

5-methoxy-1-[2-(4-nitrophenoxy)ethyl]-1H-indazol-3-ol;

1-(4-fluorophenyl)-4-(3-hydroxy-5-methoxy-1H-indazol-1-yl)butan-1-one;

N-(3,4-dimethoxyphenyl)-2-(3-hydroxy-5-methoxy-1H-indazol-1-yl)acetamide;

5-methoxy-1-(2-pyridin-2-ylethyl)-1H-indazol-3-ol hydrochloride;

5-methoxy-1-(3-pyridin-4-ylpropyl)-1H-indazol-3-ol;

1-[2,(2,4-dichlorophenyl)-2-hydroxyethyl]-5-methoxy-1H-indazol-3-ol;

5-methoxy-1-[2-1-methylpyrrolidin-2-yl)-ethyl]-1H-indazol-3-ol;

5-methoxy-1-(2-morpholin-4-ylethyl)-1H-indazol-3-ol;

5-methoxyl-1-[4-quinolin-2-ylmetoxy)-benzyl]-1H-indazol-3-ol;

5-methoxyl-1-[4-quinolin-2-ylmetoxy)-benyl]-1H-indazol-3-ol dihydrochloride;

1-(3,4-dichlorobenzyl)-1H-indazole-3,5-diol;

1-(2,4-dichlorobenzyl)-1H-indazole-3,5-diol;

1-quinolin-2-ylmethyl-1H-indazole-3,5-diol 1-(4-chlorobenzyl)-1H-indazole-3,5-diol;

5-amino-1-(2,4-dichlorobenzyl)-1H-indazol-3-ol;

5-amino-1-(4-chlorobenzyl)-1H-indazole-3-ol;

5-amino-1-(3,4-dichlorobenzyl)-1H-indazol-3-ol;

1-[1-(3,4-dichlorobenzyl)-3-hydroxy-1H-indazol-5-yl]-3-(4-methoxyphenyl)urea;

1-[1-(4-chlorobenzyl)-3-hydroxy-1H-indazol-5-yl]-3-(4-chlorophenyl)urea;

1-[1-(3,4-dichlorobenyzl)-3-hydroxy-1H-indazol-5-yl]-3-(4-chloro)phenyl)urea;

1-[1-(4-chlorobenzyl)-3-hydroxy-1H-indazol-5-yl]-3-(3,4-dichlorophenyl)urea;

1-[1-(3,4-dichlorobenzyl)-3-hydroxy-1H-indazol-5-yl]-3-(3,4-dichlorophenyl)urea;

1-[1-(4-chlorobenzyl)-3-hydroxy-1H-indazol-5-yl]-3-(4-methoxyphenyl) urea;

1-[1-(3,4-dichlorobenzyl)-3-hydroxy-1H-indazol-5-yl]-3-(4-methoxyphenyl urea;

1-[1-(2,4-dichlorobenzyl)-3-hydroxy-1H-indazol-5-yl]-3-(4-methoxphenyl urea;

1-[1-(4-chlorobenzyl)-3-hydroxy-1H-indazol-5-yl)-3-naphthalen-1-ylurea;

1-[1-(3,4-dichlorobenzyl)-3-hydroxy-1H-indazol-5-yl]-3-naphthalen-1-ylurea,

1-[1-(4-chlorobenyl)-3-hydroxy-1H-indazol-5-yl]-3-cyclohexylurea;

1-cyclohexyl-3-[1-(3,4-dichlorobenzyl)-3-hydroxy-1H-indazol-5-yl]urea;

1-cyclohexyl-3-]1-(2,4-dichlorobenzyl)-3-hydroxy-1H-indazol-5-yl]urea;

cyclopropanecarboxylic acid [1-(4-chlorobenzyl)-3-hydroxy1H-indazol-5yl]amide cyclopropanecarboxylic acid [1-(2,4-dichlorobenzyl)-3-hydroxy-1H-indazol-5-yl]amide; and 1-(4-chlorobenzyl)-5-methoxy-1H-indazole-3-thiol.

3. A salt of the compound of formula 1 of claim 1, with a mineral acid, an organic acid, or a base.

4. A pharmaceutical composition having as an active component the compound of claims 1, or 2, together with a pharmaceutically acceptable excipient.

5. The pharmaceutical composition of claim 4, in a dosage form suitable for administration, wherein said dosage form is a coated or uncoated tablet, capsule, aerosol, powder, plaster, solution, ampoule, or suppository.

6. A process for treating an allergic, asthmatic, inflamed condition of a host, or for modulating the immune system of a host, by administering to the host a pharmaceutical composition containing as active ingredient a compound of claims 1 or 2.

7. A process for preparing a compound of the formula $$\text{(I)}$$

wherein the substituents are the same as in claim 1, which comprises reacting a 5-methoxy-1H-indazol3-ol of the formula $$\text{(II)}$$

in the presence of a base and an optional diluent, with a compound of the formula $$\text{(III)}$$

to provide a compound of the formula $$\text{(IV)}$$

and recovering the product.

8. The process of claim 7, further comprising reacting the compound of formula (IV) with a hydrogen halide in the presence of a solvent, and the optional presence of a diluent, to obtain the compound of the formula

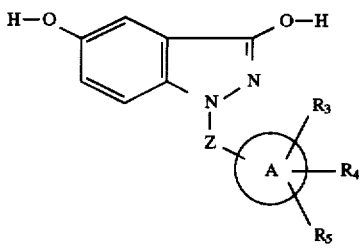

and recovering the compound of formula (V).

9. The process of claim 8, further comprising reacting the compound of formula (V) with a halogen compound of the formula R₁—Hal wherein R₁ has the same definition as in claim 1, and Hal is F, Cl, Br, or I, to obtain a compound of the formula

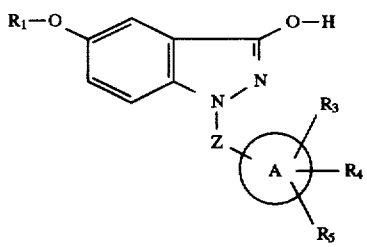

and recovering the compound of formula (VII).

10. A process for preparing a compound of the formula

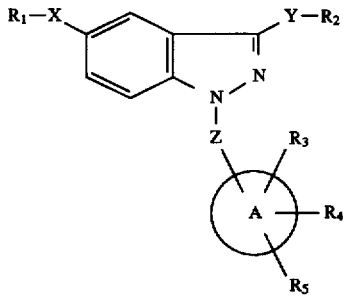

wherein the substituents are the same as in claim 1, which comprises reacting a compound of the formula

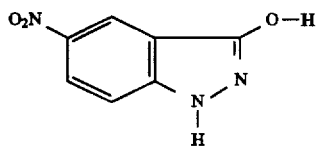

in the presence of a base and in the optional presence of a diluent, with a compound of the formula

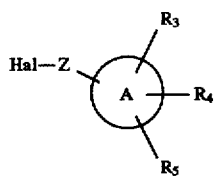

wherein Hal is F, Cl, Br, or I, to obtain a compound of the formula

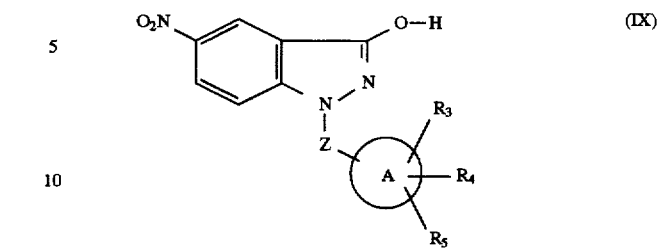

and contacting the compound of formula (IX) with a reducing agent in the presence of a catalyst and a solvent, to yield a compound of the formula

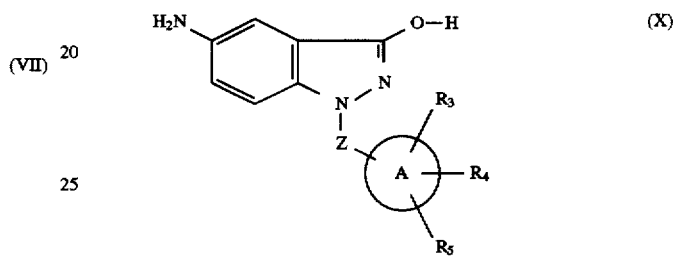

and recovering the product.

11. The process of claim 10, further comprising reacting the product of formula (X), with a compound having the formula R₁—B of formula (IX), wherein B is a halogen atom, an acid chloride, isocyanate, or chlorocarbonic residue, in the optional presence of a base and an optional diluent, to provide a compound of the formula

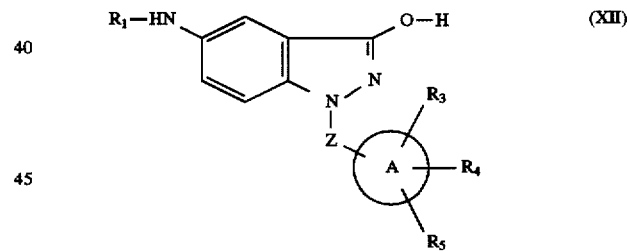

and recovering the product.

12. The process of claim 10, which comprises diazotizing and boiling the compound of formula (X) to obtain the compound of the formula

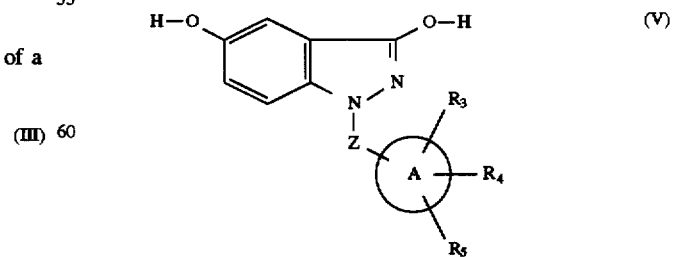

and recovering the product.

13. A process for reacting a compound of the formula
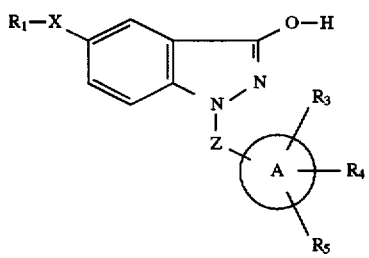 (XIII)
wherein $R_3$, $R_4$, $R_5$, A and Z are the same as in claim 1, X is O, and $R_1$ is a straight or branched $C_{1-4}$ alkyl residue, with $P_2S_5$, in the presence of a solvent, to produce a compound of the formula
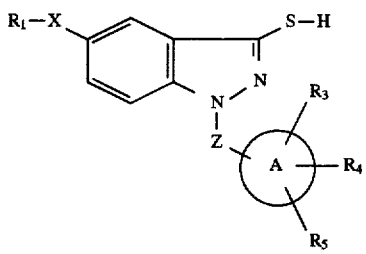 (XIV)
and recovering the product.
* * * * *

UNITED STATES PATENT AND TRADEMARK OFFICE
CERTIFICATE OF CORRECTION

PATENT NO. : 5,776,932　　　　　　　　　　Page 1 of 2
DATED    : July 7, 1998
INVENTOR(S) : Schindler, et al It is certified that error appears in the above-identified patent and that said Letters Patent is hereby corrected as shown below:

On the title page, under item [56], insert the following:

U. S. PATENT DOCUMENTS

| EXAMINER INITIAL | | PATENT NUMBER | | | | | | ISSUE DATE | PATENTEE | CLASS | SUBCLASS | FILING DATE IF APPROPRIATE |
|---|---|---|---|---|---|---|---|---|---|---|---|---|
| | | 3 | 3 | 1 | 8 | 9 | 0 | 5 | 05/09/1967 | Palazzo | | | |
| | | 3 | 4 | 7 | 0 | 1 | 9 | 4 | 09/30/1969 | Palazzo | | | |
| | | 3 | 9 | 6 | 6 | 7 | 6 | 1 | 06/29/1976 | Podesva et al. | | | |
| | | | | | | | | | | | | | |

UNITED STATES PATENT AND TRADEMARK OFFICE
CERTIFICATE OF CORRECTION

PATENT NO.   : 5,776,932
DATED        : July 7, 1998
INVENTOR(S)  : Schindler, et al It is certified that error appears in the above-identified patent and that said Letters Patent is hereby corrected as shown below:

FOREIGN PATENT OR PUBLISHED FOREIGN PATENT APPLICATION

| | | DOCUMENT NUMBER | | | | | | PUBLICATION DATE | COUNTRY OR PATENT OFFICE | CLASS | SUBCLASS | TRANSLATION YES | NO |
|---|---|---|---|---|---|---|---|---|---|---|---|---|---|
| | | 0 | 19 | 1 | 5 | 2 | 0 | A1 | 08/20/86 | EP | | | | |
| | | 0 | 19 | 9 | 5 | 4 | 3 | A2 | 10/29/86 | EP | | | | |
| | | 4 | 22 | 4 | 3 | 6 | 3 | A1 | 01/27/94 | DE | | | | |
| | | 0 | 44 | 8 | 2 | 0 | 6 | A2 | 09/25/91 | EP | | | | |
| | | | | | | | | | | | | | | |

Signed and Sealed this

Second Day of March, 1999

Attest:

Q. TODD DICKINSON

Attesting Officer

Acting Commissioner of Patents and Trademarks